(12) United States Patent
Niepa et al.

(10) Patent No.: US 11,534,408 B2
(45) Date of Patent: Dec. 27, 2022

(54) MICROCAPSULES AND METHODS OF USING THE SAME

(71) Applicant: UNIVERSITY OF PITTSBURGH—OF THE COMMONWEALTH SYSTEM OF HIGHER EDUCATION, Pittsburgh, PA (US)

(72) Inventors: Tagbo Herman Roland Niepa, Coraopolis, PA (US); Shanna-Leigh Davidson, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 516 days.

(21) Appl. No.: 16/594,878

(22) Filed: Oct. 7, 2019

(65) Prior Publication Data

US 2020/0108021 A1   Apr. 9, 2020

Related U.S. Application Data

(60) Provisional application No. 62/741,628, filed on Oct. 5, 2018.

(51) Int. Cl.
| | |
|---|---|
| *A61K 9/50* | (2006.01) |
| *A61K 35/742* | (2015.01) |
| *C12N 1/20* | (2006.01) |
| *C08G 77/12* | (2006.01) |
| *C08G 77/20* | (2006.01) |
| *C08G 77/08* | (2006.01) |

(52) U.S. Cl.
CPC .......... *A61K 9/5031* (2013.01); *A61K 9/5089* (2013.01); *A61K 35/742* (2013.01); *C08G 77/08* (2013.01); *C08G 77/12* (2013.01); *C08G 77/20* (2013.01); *C12N 1/20* (2013.01)

(58) Field of Classification Search
CPC ....... C08L 83/04; C08L 83/00; A61K 35/742; A61K 9/5089; C08G 77/08; C08G 77/12; C08G 77/20; C12N 1/20; C12N 11/04
See application file for complete search history.

(56) References Cited

U.S. PATENT DOCUMENTS 9,790,484 B2 * 10/2017 Wackett ................. C12N 11/14

OTHER PUBLICATIONS

Niepa et al. (Nature Scientific Reports 6:30578; Aug. 2016 1-9) (Year: 2016).*
Kyeong et al. (PLOS one 10.1371 (2015) 1-12). (Year: 2015).*
Wijk et al. (Chem. Commun., 2014, 50, 1542715430). (Year: 2014).*
Chang et al., "Monodisperse Emulsion Drop Microenvironments for Bacterial Biofilm Growth," Small 11(32)3954-3961 (2015).
Niepa et al., "Microbial Nanoculture as an Artificial Microniche," Scientific Reports 6:30578 (2016), 10 pages.

* cited by examiner

*Primary Examiner* — Anna R Falkowitz
(74) *Attorney, Agent, or Firm* — Baker Botts L.L.P.

(57) ABSTRACT

The present disclosure relates to microcapsules, methods of using such microcapsules in the delivery of drugs and probiotic microbes to subjects in need thereof, and methods of using such microcapsules for in vitro culture of microbes. In particular, the microcapsules comprise novel siloxane-based membranes that maintains transport properties essential to communication and growth of microbes.

14 Claims, 10 Drawing Sheets

2A

2B

3A

3B 5A 5B 5C

Figure 7

Figure 1:
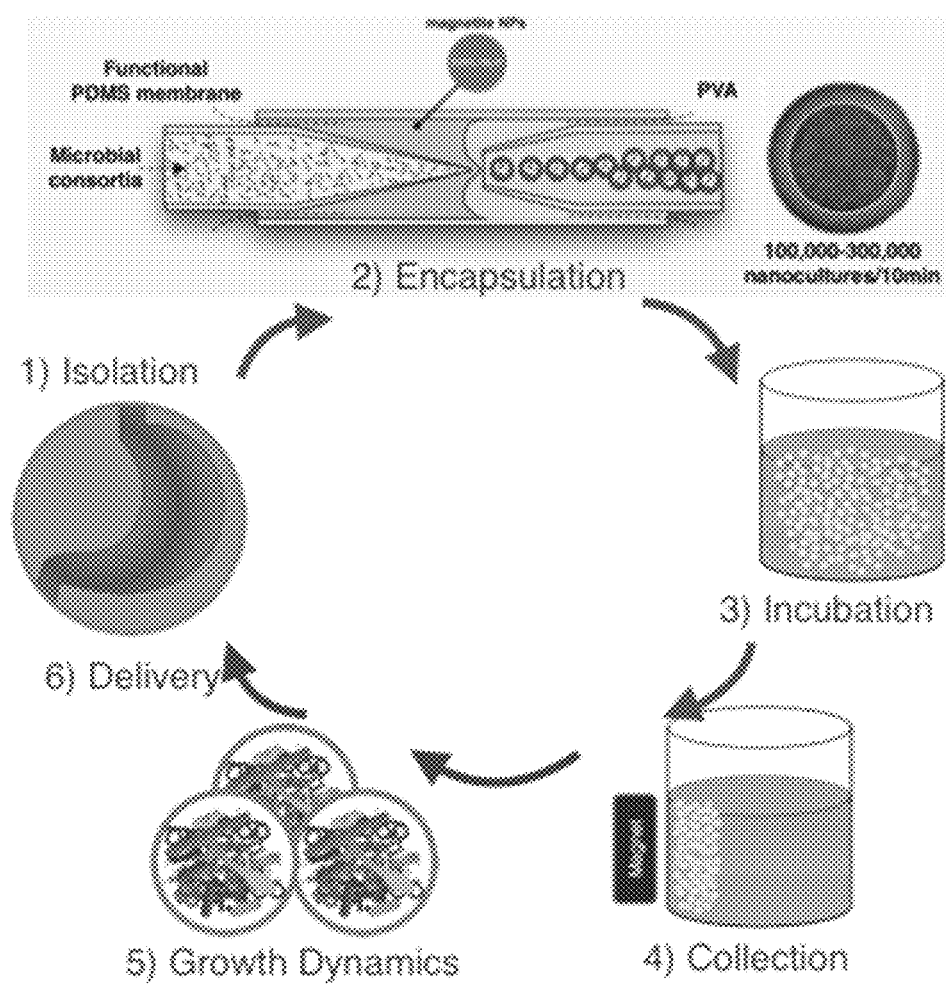

| H:V = 0.5 with Water | | |
|---|---|---|
| % DMAA in vinyl | Mean Contact Angle | % Decrease |
| 0 | 109,0 | 0% |
| 30 | 108,3 | 1% |
| 60 | 108,8 | 0% |
| 70 | 108,6 | 0% |
| 80 | 108,5 | 0% |
| 90 | 107,5 | 1% |

| H:V = 0.5 with Ethanol | | |
|---|---|---|
| % DMAA in vinyl | Mean Contact Angle | % Decrease |
| 0 | 18,2 | 0% |
| 30 | 32,6 | -79% |
| 60 | 35,0 | -93% |
| 70 | 34,4 | -90% |
| 80 | 30,4 | -67% |
| 90 | 30,6 | -69% |

| H:V = 1 with Water | | |
|---|---|---|
| % DMAA in vinyl | Mean Contact Angle | % Decrease |
| 0 | 107,7 | 0% |
| 30 | 107,5 | 0% |
| 60 | 103,4 | 4% |
| 70 | 102,1 | 5% |

| H:V = 1 with Ethanol | | |
|---|---|---|
| % DMAA in vinyl | Mean Contact Angle | % Decrease |
| 0 | 36,6 | 0% |
| 30 | 37,1 | -1% |
| 60 | 29,8 | 19% |
| 70 | 29,9 | 19% |

9A

9B

9C

MICROCAPSULES AND METHODS OF USING THE SAME

CROSS-REFERENCE TO RELATED APPLICATIONS

This application claims priority to U.S. Provisional Application No. 62/741,628, filed Oct. 5, 2018, to which priority is claimed and the contents of which are incorporated herein by reference in their entireties.

1. INTRODUCTION

The present disclosure relates to microcapsules, methods of using such microcapsules in delivery of drugs and probiotic microbes to subjects in need thereof, and methods of using such microcapsules for in vitro culture of microbes. In particular, the microcapsules comprise novel siloxane-based membranes that maintains transport properties essential to communication and growth of microbes.

2. BACKGROUND

*Clostridium difficile* infection (CDI) has grown to become a common health care associated infection, attributing to approximately $5 billion in annual costs to the U.S. health care system. According to the CDC, at least half a million patients were treated for primary CDI in 2011, with 29,300 of those primary infections resulting in death. A substantial problem with CDI is the high occurrence of re-infection (13-50% of patients) after treatment, contributing to the overall burden of disease. Following the first recurrence of CDI and treatment, the probability of a second, third and fourth recurrence of infection decreases substantially (38%, 29%, and 27%, respectively); however, multiple recurring infections become significantly more difficult to treat. Furthermore, in some cases infection is untreatable, resulting in "Complicated CDI", which leads to at least one complication such as hypotension requiring vasopressors, ileus, toxic megacolon and death.

Primary CDI is commonly treated with antibiotics; namely vancomycin, metronidazole and fidaxomicin, with success rates ranging between 70% to 90%. However, the efficacy of antibiotic treatment for recurring CDI infections drops significantly and becomes suboptimal. In lieu of this, an alternative therapy called Fecal Microbiota Transplant (FMT) has emerged.

FMT involves a fecal transplant from a healthy donor, the sample of which has been screened and treated into a liquid suspension that is administered as an enema. Other options include colonoscopy, or a nasogastric tube; however, both options have been determined to cause the patient significant discomfort. Hence, an enema is regarded as giving the highest comfort level in combination with satisfying results of efficacy. FMT is an important option in treating recurring CDI. However, it still has many shortcomings. There are yet to be studies done examining the long-term safety and efficacy of FMT, which could later result in the development of more severe ailments, such as cancer, metabolic diseases and complications, as well as auto-immune diseases.

Furthermore, much like blood, the donor stool sample is constrained under intense limitations, and must undergo rigorous screening to be accepted as a donation. Stool (and blood) samples must be deemed free from a long list of potential transmittable diseases, and furthermore, the donor must also go through a preliminary interview, whereby the same standard requirements for blood donation is upheld for stool donation. For example, individuals who have a history of, or known exposure to, HIV, HBV or HCV, as well as malaria or tuberculosis, are not eligible to donate. Likewise, use of illegal drugs, and any recent (<6 months) needle stick accident, as well as body tattoos, piercings, and acupuncture, deem an individual ineligible to donate. Healthcare workers are similarly excluded, to avoid the risk of transmitting antibiotic-resistant organisms. This significantly limits who can donate, and as such makes it difficult, in many instances, to obtain a fresh sample for FMT. Furthermore, though the samples go through rigorous testing, there is still a possibility of an accidental transmission of opportunistic pathogens into the recipient-only in the last two years has there been a test developed for prions, for example, and this is still being tested for efficacy in larger sample sizes, and not yet commercially available. This is extremely problematic in severe cases of CDI, as the risk of morbidity is substantially higher, and may prove fatal. Instead of fresh samples, frozen samples are now being tested for efficacy, which, while it will appease the demand for fresh samples, remains problematic for the patient, as success of the treatment depends on the patient holding in the infused material. Side-effects of FMT include abdominal pain, transient diarrhea, excessive flatulence, nausea and slight fever.

*Clostridium difficile*, an obligate anaerobe, remains an elusive pathogen in the lab, where it is difficult to culture without the exact environment it requires, much like many microorganisms taking up residence in the gut. Thus, it is quite challenging to reconstruct a healthy microbiome that has been wiped out after chemical insults, such as a strong antibiotic treatment.

Prior attempts of growing microbes were made in water-oil-water double emulsion (Chang et al., Small, 2015 Aug. 26; 11(32):3954-61). A microbial nanoculture system was previously developed with many limitations, including uncontrolled transport properties (Niepa T H et al., Scientific Report, 2016 Aug. 1; 6:30578).

Thus, there remains a need in the art for an improved method for culturing and delivering microbes to a subject. The presently disclosed addresses this need as discussed in detail below.

3. SUMMARY

The present disclosure provides microcapsules comprising novel siloxane-based membranes.

In one aspect, the present disclosure provides a microcapsule comprising: (a) a membrane comprising a cross-linked polymer, wherein the polymer comprises siloxane units; and (b) a core comprising a plurality of microbes suspended in a medium, wherein the core is completely enclosed by the membrane. In certain embodiments, the polymer is a copolymer. In certain embodiments, the copolymer is a methylhydrosiloxane and dimethylsiloxane copolymer.

In certain embodiments, the membrane further comprises a silica nanoparticle. In certain embodiments, the membrane incorporates magnetite nanoparticles. In certain embodiments, the siloxane units are hydrosiloxane units, e.g., methylhydrosiloxane units. In certain embodiments, the polymer is a poly(hydrosiloxane) polymer. In certain embodiments, the polymer is generated by crosslinking a starting material. In certain embodiments, the starting material comprises a methylhydrosiloxane (HMS) and a vinyl terminated polydimethylsiloxane (DMS). In certain embodiments, the HMS is (4-6% methylhydrosiloxane)-dimethylsiloxane copolymer, trimethylsiloxane terminated. In certain embodiments, the vinyl terminated polydimethylsiloxane comprises 0.8-1.2 wt % vinyl and has a molecular weight (MW) of about 6000 g/mol. In certain embodiments, the starting material comprises hydride groups and vinyl groups, wherein the ratio of the hydride groups to the vinyl groups is between about 0.5 and about 1.

In certain embodiments, the membrane further comprises a ferromagnetic material. In certain embodiments, the ferromagnetic material comprises magnetite.

In certain embodiments, the polymer is crosslinked with dimethylallylamine (DMAA). In certain embodiments, the polymer is generated by crosslinking a starting material comprising dimethylallylamine as a crosslinking agent, wherein the dimethylallylamine is present in a concentration of between about 0% and about 30% of total vinyl group in the starting material. In certain embodiments, the DMAA is in a concentration of about 1%, about 5%, about 10%, about 15%, about 20%, about 25%, or about 30% of total vinyl group in the starting material.

In certain embodiments, the plurality of microbes is obtained from a mammal. In certain embodiments, the plurality of microbes is obtained from a human. In certain embodiments, the microbes are obtained from lungs, respiratory tracts, genital tracts, skin, eyes or nasal passages of the mammal. In certain embodiments, the plurality of microbes is obtained from soil or marine. In certain embodiments, the microbes comprise probiotic microbes.

In certain embodiments, the present disclosure provides a method of making a polymer, comprising mixing a methylhydrosiloxane, a vinyl-terminated polydimethylsiloxane base and a platinum catalyst to form a mixture, then incubating the mixture to form the polymer. In certain embodiments, the mixture further comprises a crosslinking agent, e.g., dimethylallylamine.

In certain embodiments, the mixture is incubated at about 70° C. for about 5 minutes. In certain embodiments, the concentration of the platinum catalyst is about 3 ppm in the mixture.

In certain embodiments, the present disclosure provides a membrane comprising the polymer made from the methods disclosed herein.

In certain embodiments, the present disclosure provides a microcapsule comprising: (a) a membrane comprising the polymer made from the methods disclosed herein; and (b) a core comprising a plurality of microbes suspended in a medium, wherein the core is completely enclosed by the membrane.

In another aspect, the present disclosure provides a method for restoring a healthy microbiome in a subject, comprising administering to the subject a plurality of microcapsules comprising an effective amount of probiotic microbes, wherein each of the microcapsule comprises: (a) a membrane comprising a crosslinked polymer, wherein the polymer comprises siloxane units; and (b) a core comprising a plurality of the probiotic microbes suspended in a medium, wherein the core is completely enclosed by the membrane.

In certain embodiments, the probiotic microbes are obtained from the subject before the subject receives an antibiotic treatment. In certain embodiments, the plurality of microcapsules is administered to the subject after the subject receives the antibiotic treatment.

In certain embodiments, subject is a mammal. In certain embodiments, subject is a human. In certain embodiments, the probiotic microbes are obtained from lungs, respiratory tracts, genital tracts, skin, eyes or nasal passages of the subject.

In certain embodiments, the subject is susceptible to or suffers from *Clostridium Difficile* Infection (CDI). In certain embodiments, suffers from an immune-compromised disorder or is an elderly patient. In certain embodiments, the subject is obese. In certain embodiments, the plurality of microcapsules is administered to the subject orally. In certain embodiments, the subject is a human.

In certain embodiments, the membrane further comprises a silica nanoparticle. In certain embodiments, the siloxane units are hydrosiloxane units. In certain embodiments, the polymer is a poly(hydrosiloxane) polymer.

In another aspect, the present disclosure provides a method for culturing microbes in vitro, comprising: (a) obtaining a plurality of microbes; (b) encapsulating the plurality of microbes into a microcapsule, wherein the microcapsule comprises: (i) a membrane comprising a crosslinked polymer, wherein the polymer comprises siloxane units, and (ii) a core comprising the plurality of microbes suspended in a medium, wherein the core is completely enclosed by the membrane; and (c) culturing the microcapsule in a suitable condition allowing the growth of the microbes.

In certain embodiments, the membrane further comprises a silica nanoparticle. In certain embodiments, the siloxane units are hydrosiloxane units. In certain embodiments, the polymer is a poly(hydrosiloxane) polymer. In certain embodiments, the plurality of microbes is obtained from a mammal. In certain embodiments, the plurality of microbes is obtained from a human. In certain embodiments, the microbes are obtained from gum of the mammal. In certain embodiments, the microbes are obtained from lungs, respiratory tracts, genital tracts, skin, eyes or nasal passages of the mammal. In certain embodiments, the microbes are obtained from soil or marine. In certain embodiments, the membrane comprises magnetite nanoparticles to recover the microcapsules.

In another aspect, the present disclosure provides a pharmaceutical composition for use in restoring a healthy microbiome in a subject comprising a plurality of microcapsules comprising an effective amount of probiotic microbes, wherein each of the microcapsule comprises: (a) a membrane comprising a crosslinked polymer, wherein the polymer comprises siloxane units; and (b) a core comprising a plurality of the probiotic microbes suspended in a medium, wherein the core is completely enclosed by the membrane. In certain embodiments, the pharmaceutical composition disclosed herein further comprises an acceptable carrier.

In another aspect, the present disclosure provides a kit comprising a plurality of microcapsules disclosed herein. In another aspect, the present disclosure provides a kit comprising a pharmaceutical composition disclosed herein.

4. BRIEF DESCRIPTION OF THE DRAWINGS

FIG. 1 provides a diagram showing an embodiment of the steps of making and delivering microbial-based therapeutic nanoculture capsule to a subject.

Figure 2A:
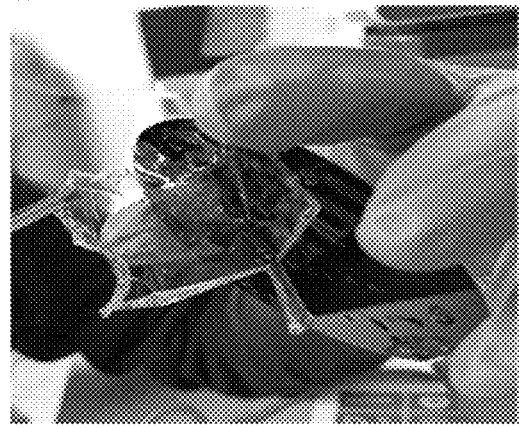
Figure 2B:
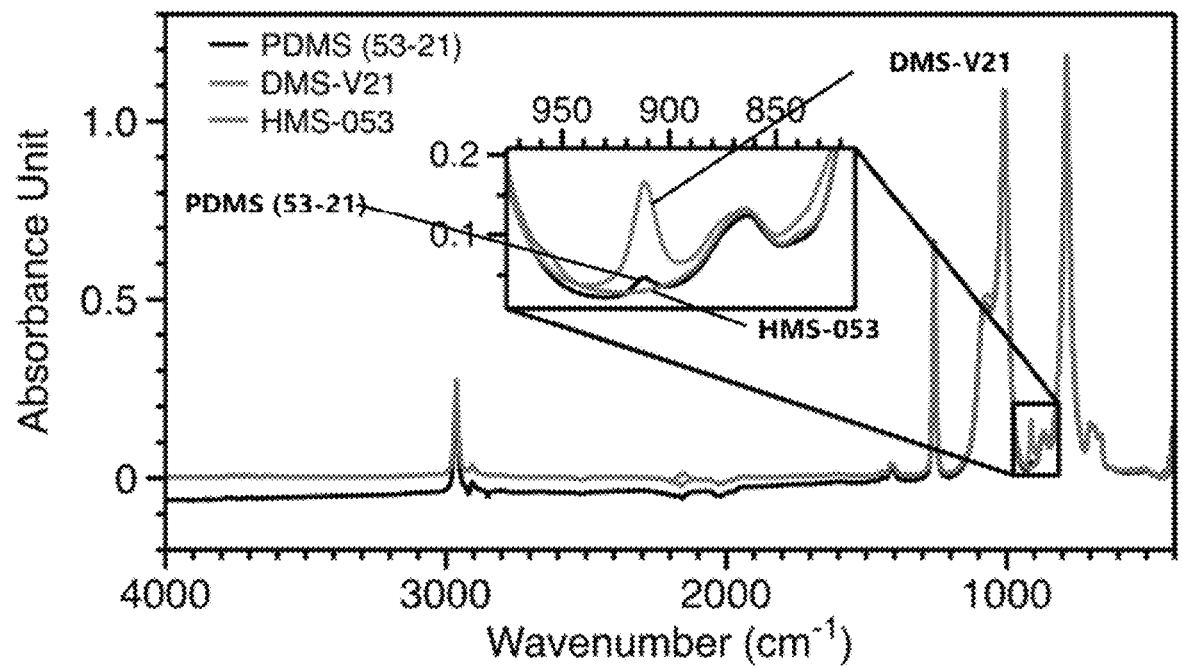

FIGS. 2A-2B provide properties of an embodiment of the presently disclosed membrane that forms the presently disclosed microcapsules. (2A) A representative image of an embodiment of the presently disclosed membrane. (2B) Representative data of IR-spectra on fully cured membrane PDMS (53-21), DMS-V21, and HMS-053. Enlarged window shows the peak of interest at approximately 910 cm', which indicates the vinyl C=C double bond. PDMS (53-21) (Polydimethylsiloxane 53-21) was the polymer product generated from of HMS-053 (Methylhydrosiloxane-053) and DMS-V21 (Vinyl Terminated Polydimethylsiloxane-V21), with the use of a platinum catalyst to induce crosslinking and hence the curing of the polymer.

Figure 3A:
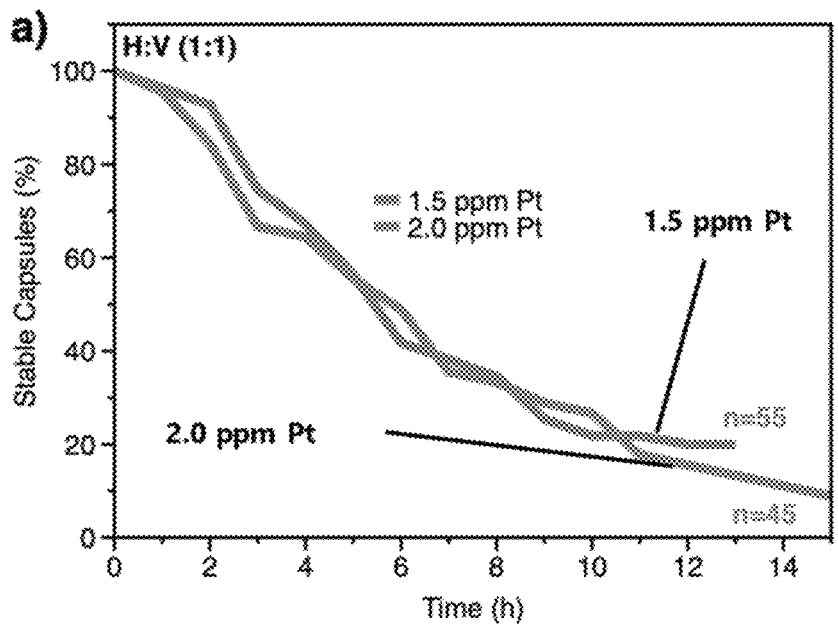
Figure 3B:
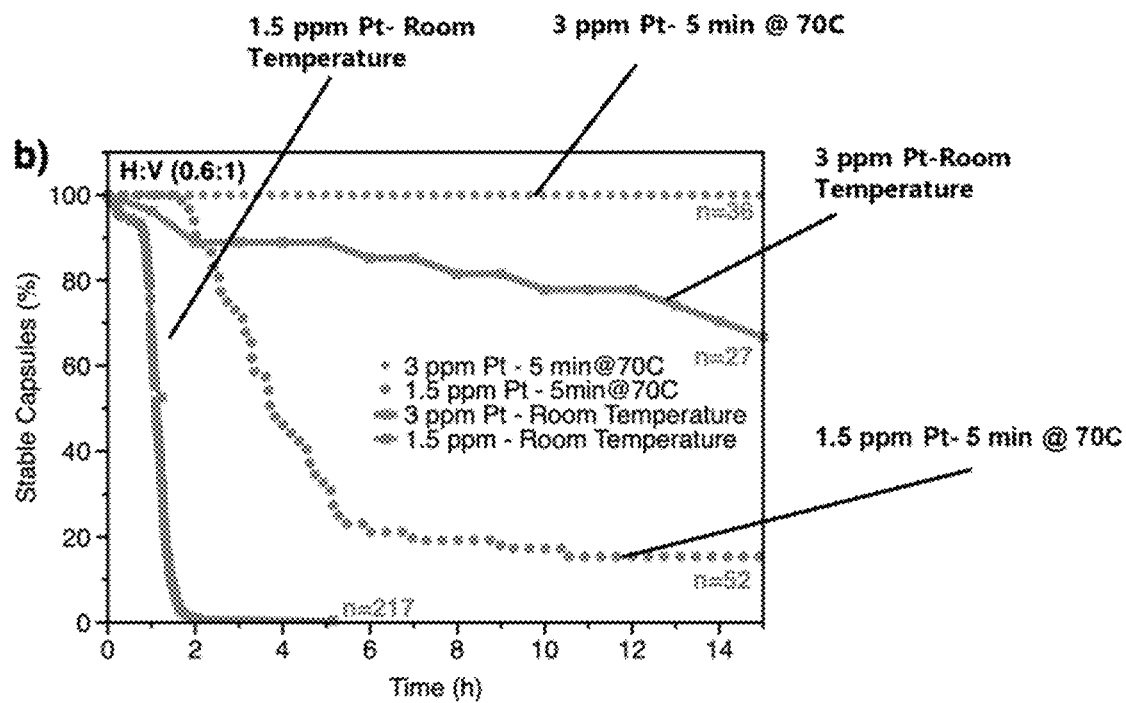
Figure 3C:
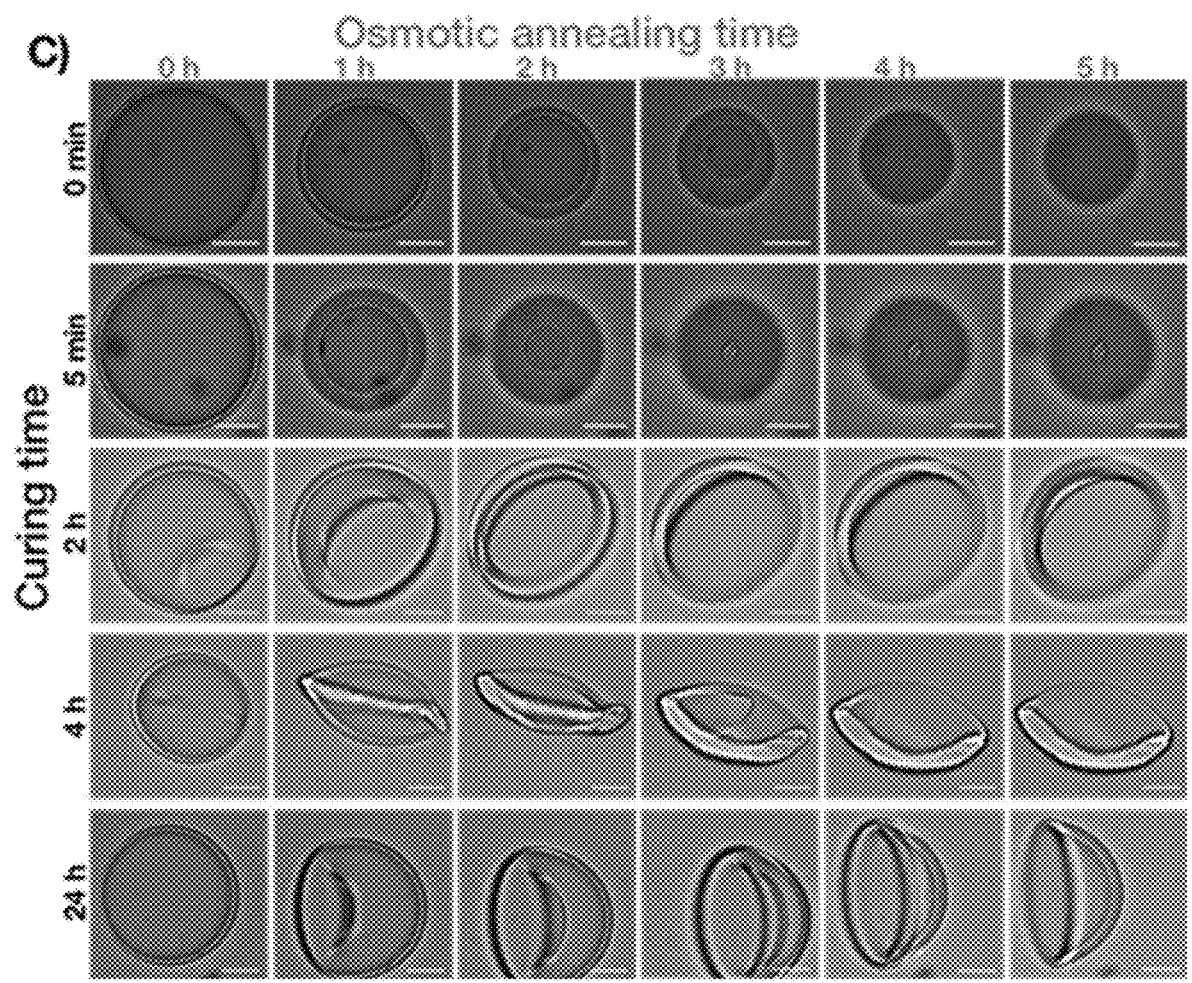

FIGS. 3A-3C provide assessment of the stability of the presently disclosed nanoculture capsules (also called microcapsules in the present disclosure). H:V represents the ratio of hydride to vinyl functional groups in the starting material for producing the presently disclosed polymer. (3A) Stability was measured in nanoculture capsules treated with 1.5 ppm platinum catalyst or 2.0 ppm platinum catalyst. H:V= (1:1). (3B) Stability was measured in nanoculture capsules treated with 1.5 ppm platinum catalyst or 3 ppm platinum catalyst, either with heat treatment at 70° C. for 5 minutes, or note. H:V=(0.6:1). (3C) Representative brightfield images of nanoculture capsules at different timepoints of curing time and osmotic annealing time. The capsules were cured for different amounts of time at 70° C., and then were exposed to a 1 M NaCl solution, a hypertonic environment which caused water to osmose out of the capsules. Scale bar=50 μm.

Figure 4:
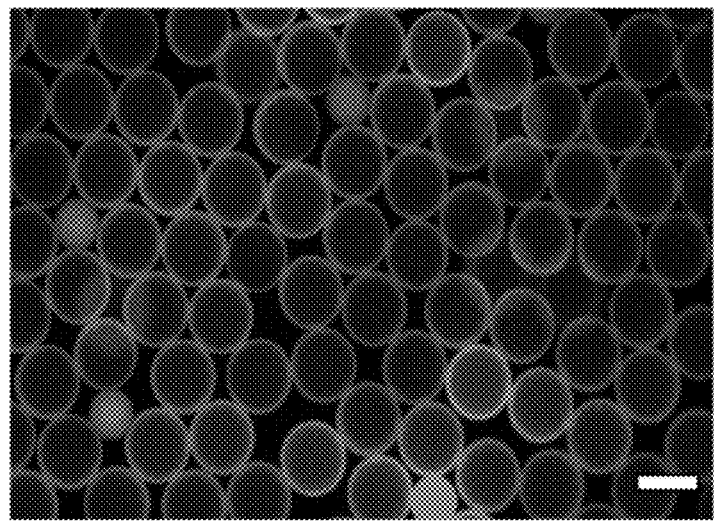

FIG. 4 provides a representative fluorescent image (10×) of an embodiment of the presently disclosed nanoculture capsules. Scale bar: 200 μm.

Figure 5A:
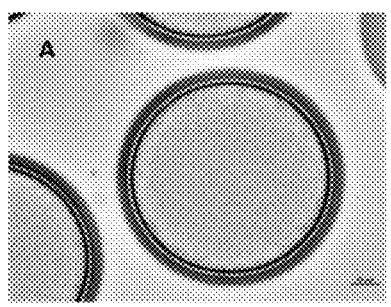
Figure 5B:
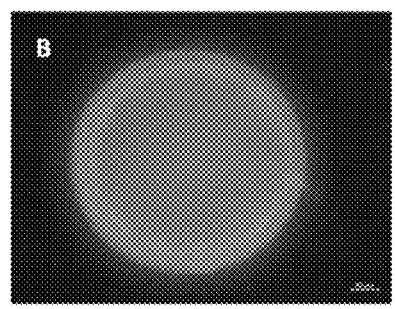
Figure 5C:
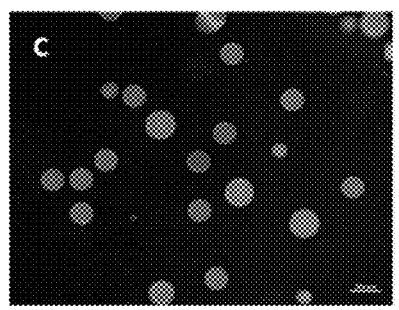

FIGS. 5A-5C provide growth dynamics of microorganisms encapsulated in an embodiment of the presently disclosed nanoculture capsules. (5A) A representative brightfield image (50×) showing confluent growth of *Escherichia coli* within the capsules. Scale bar: 20 μm. (5B) A representative fluorescent image (50×) showing confluent growth of *Escherichia coli* within the capsules. Scale bar: 20 μm. (5C) A representative fluorescent image (5×) showing confluent growth of *Escherichia coli* within the capsules. Scale bar: 200 μm.

Figure 6:
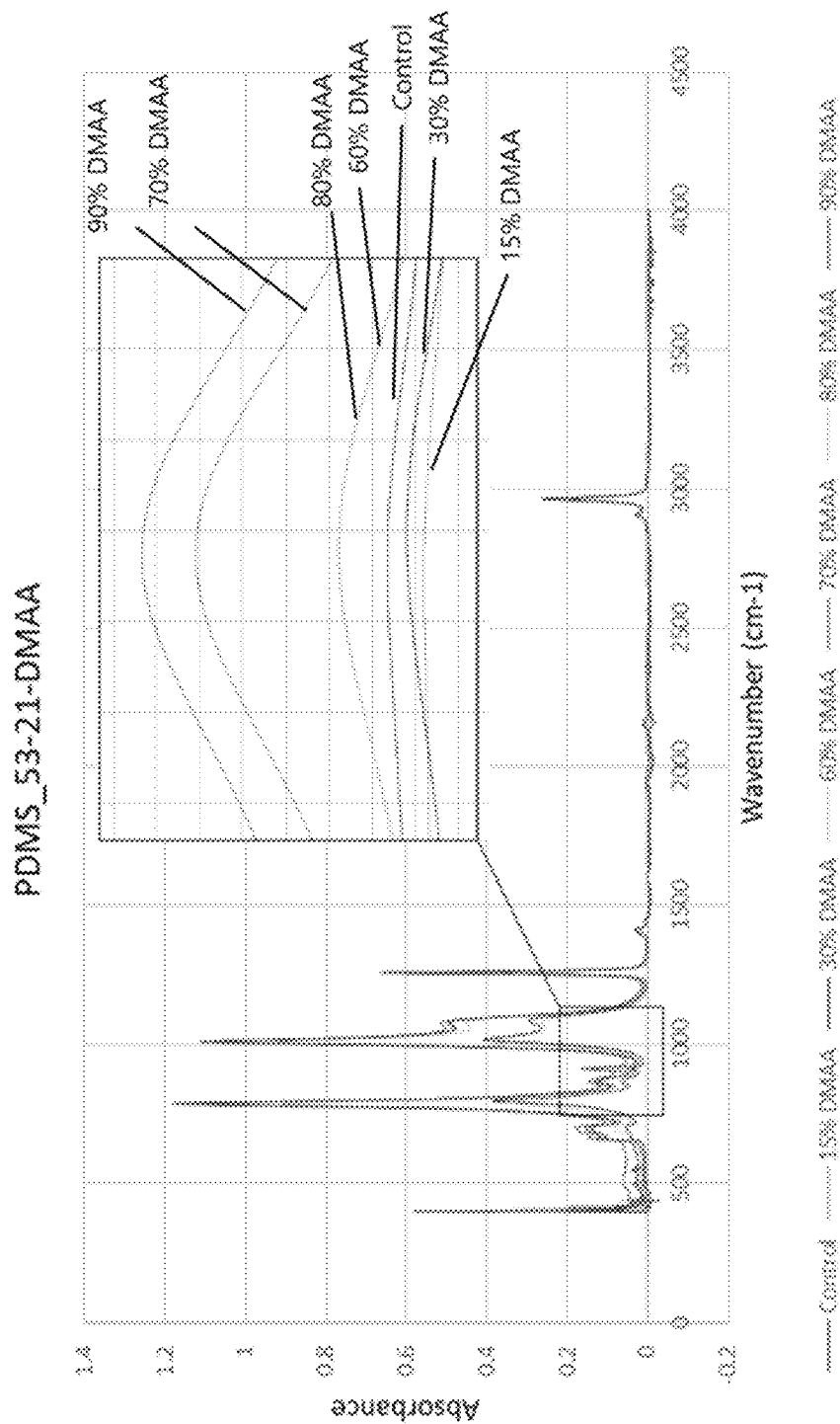

FIG. 6 provides IR-spectra measurements of the presently disclosed nanoculture capsules having 15%, 30%, 60%, 70%, 80%, or 90% dimethylallylamine (DMAA). Control nanoculture capsules includes 0% DMAA in the membrane. % DMAA represents the percentage ratio of moles of vinyl functional group of DMAA to the total moles of vinyl functional group in the starting material (DMAA+DMS-V21).

FIG. 7 provides measurements of contact angle in the presently disclosed nanoculture capsules having different H:V ratios and % DMAA. Water and ethanol were used as liquid phase solvents. Contact angle measurements indicated the wettability of the nanoculture capsules.

Figure 8:
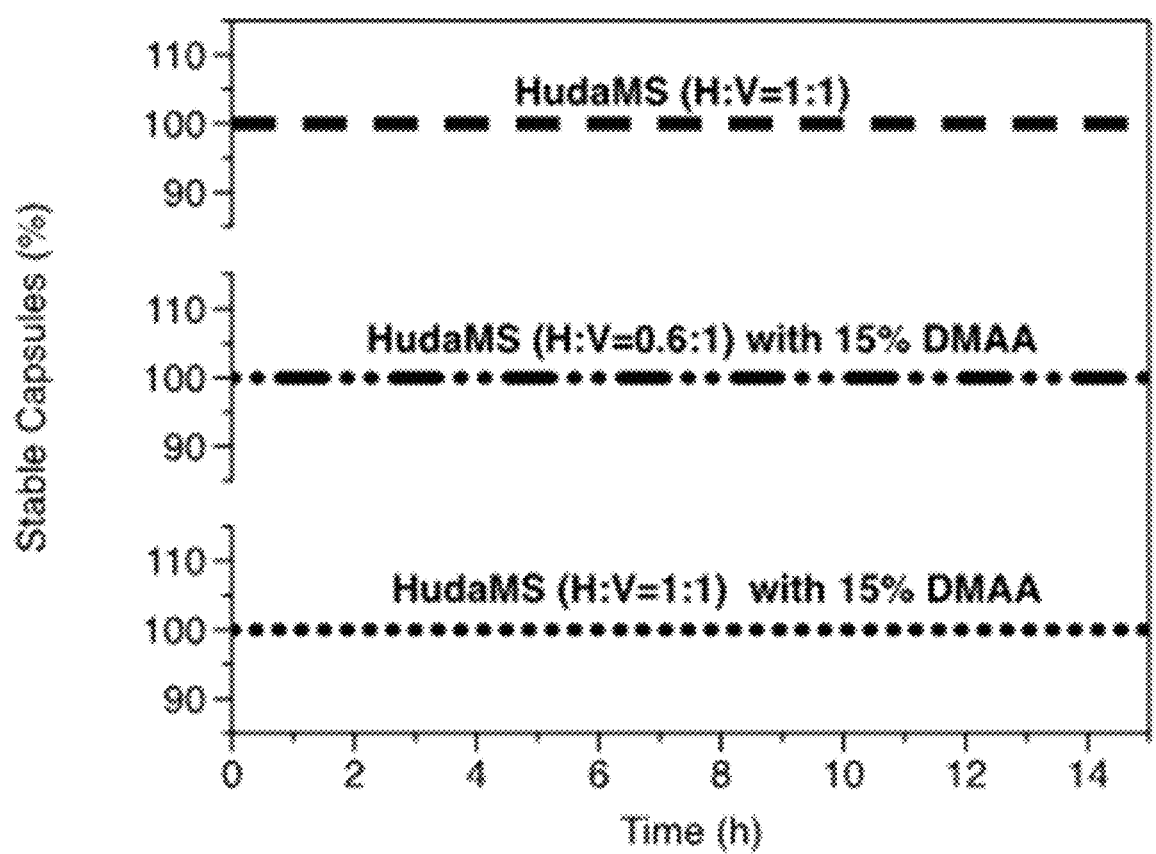

FIG. 8 provides stability measurements of the presently disclosed nanoculture capsules having different H:V ratios and % DMAA.

Figure 9A:
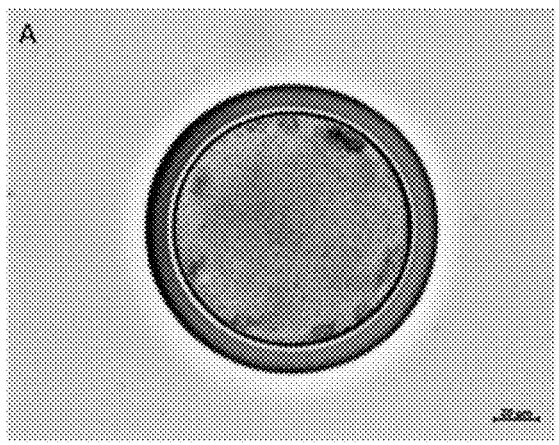
Figure 9B:
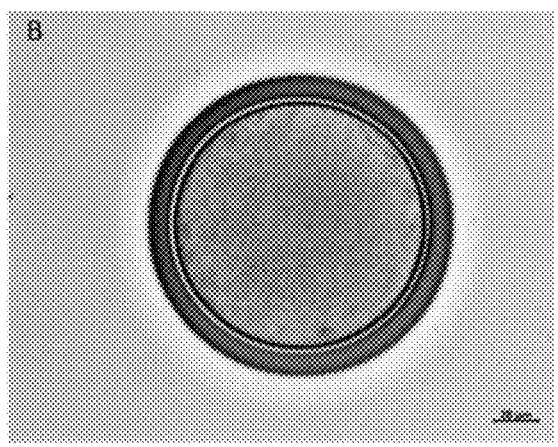
Figure 9C:
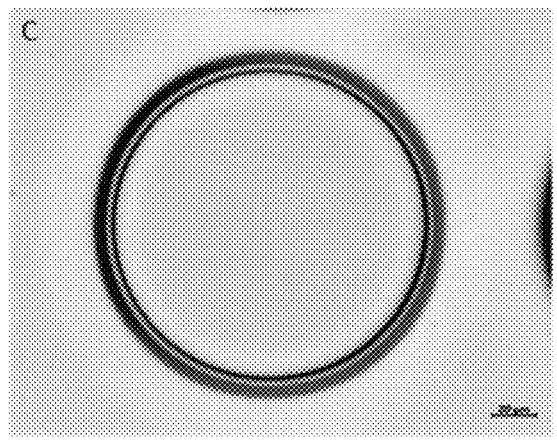

FIGS. 9A-9C provide representative brightfield images of the presently disclosed nanoculture capsules. *Pseudomonas aeruginosa* PAO1 strain was used as the bacterial inoculum for the inner phase of the capsules. Antibiotics, including tobramycin and tetracycline, were introduced 24 hours after encapsulation. (9A) Untreated PAO1 nanoculture after 24 hours. (9B) PAO1 nanoculture treated with 50 ug/ml tobramycin. (9C) PAO1 nanoculture treated with 50 ug/ml tetracycline.

5. DETAILED DESCRIPTION

The present disclosure relates to microcapsules, methods of using such microcapsules in the delivery of drugs and probiotic microbes to subjects in need thereof, and methods of using such microcapsules for in vitro culture of microbes. In particular, the microcapsules comprise novel siloxane-based membranes that maintains transport properties essential to communication and growth of microbes. The microcapsules disclosed herein can be used for safe delivery of beneficial microbial community (e.g., probiotics), growing unculturable microbes, and performing in situ study of microbial dynamics by growing microbes in native conditions and environments. Non-limiting embodiments of the invention are described by the present specification and Examples.

5.1 Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "microbe" or "microorganism" encompasses bacteria, archaea, fungi, protists, viruses, and microscopic animals that can be found living in water, soil, air, and other living organisms, such as mammals and humans.

As used herein, the term "bacteria" encompasses both prokaryotic organisms and archaea present in mammalian microbiota. The terms "intestinal microbiota", "gut flora", and "gastrointestinal microbiota" are used interchangeably to refer to bacteria in the digestive tract. The terms "saliva microbiota," "saliva flora," "mouth microbiota," and "mouth flora" are used interchangeably to refer to bacteria found in the oral cavity.

As used herein, a "culture" of microbes (e.g., bacteria) can refer to an in vitro culture of at least one microbe species. Such microbes can be cultured with one or more activators or repressors. As used herein, the terms "activators" and "repressors" refer to agents that increase or decrease the number and/or activity and/or metabolism of one or more desired microbes, respectively.

As used herein, the term "probiotic composition" or "probiotic" can refer to a composition containing at least one species, genus, family, strain, order, or class of bacteria (e.g., a single isolate or a combination of desired bacteria), and can also include any additional carriers, excipients, and/or therapeutic agents that can be administered to a mammal. Probiotic microbes are microorganisms that have health benefits. Probiotic microbes can be administered with a buffering agent to allow the bacteria to survive in the acidic environment of the stomach, that is, the bacteria resist low pH and are able to survive passage through the stomach to colonize and grow in the intestinal milieu. Buffering agents can include, for example, sodium bicarbonate, milk, yoghurt, infant formula, and other dairy products.

A "microbiome" can refer to the totality of microbes and their genetic elements (genomes) from a defined environment. A defined environment can, for example, be the intestine and/or the oral cavity of a human being. Thus, microbiome can include all area-specific microbiota and their complete genetic elements.

An "individual" or "subject" herein is a vertebrate, such as a human or non-human animal, for example, a mammal. Mammals include, but are not limited to, humans, non-human primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

As used herein, the term "disease" refers to any condition or disorder that damages or interferes with the normal function of a cell, tissue, or organ.

An "effective amount" of a substance as that term is used herein is that amount sufficient to effect beneficial or desired results, including clinical results, and, as such, an "effective amount" depends upon the context in which it is being applied. An effective amount can be administered in one or more administrations.

As used herein, and as well-understood in the art, "treatment" is an approach for obtaining beneficial or desired results, including clinical results. For purposes of this subject matter, beneficial or desired clinical results include, but are not limited to, alleviation or amelioration of one or more sign or symptoms, diminishment of extent of disease, stabilized (i.e., not worsening) state of disease, prevention of disease, delay or slowing of disease progression, and/or amelioration or palliation of the disease state. The decrease can be a 10%, 20%, 30%, 40%, 50%, 60%, 70%, 80%, 90%, 95%, 98% or 99% decrease in severity of complications or symptoms. "Treatment" can also mean prolonging survival as compared to expected survival if not receiving treatment.

As used herein, the term "in vitro" refers to an artificial environment and to processes or reactions that occur within an artificial environment. In vitro environments exemplified, but are not limited to, test tubes and cell cultures.

5.2 Microcapsules

In one aspect, the present disclosure provides microcapsules comprising (a) a membrane and (b) a core, wherein the core is completely enclosed by the membrane.

In certain embodiments, the membrane comprises a crosslinked polymer. In certain embodiments, the polymer is a co-polymer. In certain embodiments, the polymer comprises a repeated unit that is selected from the non-limiting group consisting of silanes, heterosilanes, siloxanes, hydrosiloxane, silazanes, silathianes, and silicones, as well as combinations thereof. For example, in certain embodiment, the membrane comprises a copolymer of methylhydrosiloxane and dimethylsiloxane. In certain embodiments, the ratio of methyl to vinyl functional groups in silanes or silicones is varied to optimize the crosslinking density, in terms of gaps and spaces within the membrane.

In certain embodiments, the polymer is generated by crosslinking starting materials. In certain embodiments, varying the ratio of the functional groups of the starting materials that generate the polymer modifies the elastomeric properties of the membrane. Non-limiting examples of elastomeric properties of the membrane include brittleness and elasticity of the membrane. In certain embodiments, the functional groups include methyl groups, hydride groups, vinyl groups, and combinations thereof. In certain embodiments, the ratio of functional groups includes the ratio of hydride groups to vinyl groups and the ratio f methyl groups to vinyl groups. In certain embodiments, increasing the ratio of hydride groups to vinyl groups or the ratio of methyl groups to vinyl groups in the starting materials increases the saturation of vinyl bonds and the occurrence of crosslinking, thus increasing the brittleness and reducing the elasticity of the membrane. In certain embodiments, reducing the ratio of hydride groups to vinyl groups or the ratio of methyl groups to vinyl groups in the staring material decreases the saturation of vinyl bonds and the occurrence of crosslinking, thus decreasing the brittleness and increasing the elasticity of the membrane. In certain embodiments, the ratios between the functional groups in the starting materials is modified by varying the concentrations of the starting materials for making the membrane.

In certain embodiments, the starting material comprises a methylhydrosiloxane (HMS), a vinyl terminated polydimethylsiloxane (DMS), or a combination thereof. In certain embodiments, the starting material comprises a combination of HMS and DMS. An exemplary HMS is methylhydrosiloxane, dimethylsiloxane copolymer, trimethylsiloxane terminated. Any suitable HMS and DMS known in the art can be used with the presently disclosed subject matter. In certain embodiments, the HMS is (4-6% methylhydrosiloxane)-dimethylsiloxane copolymer, trimethylsiloxane terminated, corresponding to CAS No. 68037-59-2 (commercially available from, e.g., Gelest, Morrisville, Pa. as catalogue no. HMS-053). In certain embodiments, the DMS is a vinyl terminated polydimethylsiloxane comprising 0.8-1.2 wt % vinyl and having a molecular weight of about 6,000 g/mol, corresponding the compound of CAS No. 68083-19-2 (commercially available from, e.g., Gelest, Morrisville, Pa. as catalogue no. DMS-V21). In certain embodiments, the HMS comprises the functional group of hydride and/or methyl. In certain embodiments, the DMS comprises the functional group of vinyl.

In certain embodiments, the ratios between functional groups are adjusted by adjusting the concentrations of the starting materials (e.g., by adjusting the ratio of HMS to DMS). In certain embodiments, HMS is used as a reducing agent in the crosslinking reaction, and the hydrogen functional group provided by HMS acts as a proton donor. In certain embodiments, DMS provides the vinyl functional group in the crosslinking reaction.

In certain embodiments, the ratio of hydride groups to vinyl groups or methyl groups to vinyl groups in the starting material is between about 0.5 and about 1 (e.g., about 0.5, about 0.6, about 0.7, about 0.8, about 0.9, or about 1). In certain embodiments, the ratio of hydride groups or methyl groups to vinyl groups is between 0.6 and 1. In certain embodiments, the ratio of hydride groups or methyl groups to vinyl groups is about 0.5 or about 1. In certain embodiments, the ratio of hydride groups or methyl groups to vinyl groups is 0.6 or 1.

In certain embodiments, additional functional groups are added onto the silicon backbone in the form of crosslinkers, to tune the membrane properties, such as wettability, hydrophobicity and hydrophilicity, oleophobicity, as well as the reactivity of the membrane with specific molecules. In certain embodiments, the functional groups are selected from the group consisting of amines, ketones, and benzenes rings that common functional groups in antibiotics, and addition of such functional groups improves the permeability of the drugs that are currently in use to fight bacterial infection. In certain embodiments, the membrane further comprises silica nanoparticles, which enables the microcapsules to withstand high shear stress similar to environmental conditions while maintain transport properties essential to communication and growth.

In certain embodiments, the membrane further comprises N,N-dimethylallylamine, also referred to herein simply as dimethylallylamine or DMAA. In certain embodiments, the dimethylallylamine is added to the starting material as a crosslinking agent before curing for crosslinking with other components of the starting material. Dimethylallylamine has the molecular formula $CH_2=CHCH_2N(CH_3)_2$ and the following chemical structure:

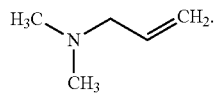

In certain embodiments, inclusion of dimethylallylamine as a crosslinking agent in the polymer of the membrane decreases the hydrophobicity and increases the hydrophilicity of the membrane. Increasing hydrophilicity can promote the permeability and diffusion properties of the membrane, thus assisting in studying the communication signals between the internal and external environments of the microcapsules.

In certain embodiments, the membrane comprises dimethylallylamine. In certain embodiments, dimethylallylamine is used as a crosslinking agent during the curing of the polymer. In certain embodiments, the starting material comprises dimethylallylamine. In certain embodiments, dimethylallylamine is present in a concentration of from about 10% and about 90% (e.g., about 10%, about 20%, about 30%, about 40%, about 50%, about 60%, about 70%, about 80%, about 90%) of the total vinyl group content in the starting material. In certain embodiments, the concentration is the percentage of mole of vinyl groups (or amine group) of dimethylallylamine in total number of moles of vinyl groups in the starting material. The total number of moles of vinyl groups in the starting material is the number of moles of vinyl groups of DMS plus the number of moles of vinyl group of dimethylallylamine. In certain embodiments, the membrane comprises dimethylallylamine in a concentration of about 10%, about 15%, about 20%, about 25%, about 30%, about 35%, about 40%, about 45%, about 50%, about 60%, about 70%, about 80%, about 90%, or about 95% of total vinyl in the starting material.

In certain embodiments, the membrane further comprises a ferromagnetic material. Including a ferromagnetic material into the membrane of the presently disclosed microcapsules allows the movement of the microcapsules to be controlled with the use of magnetic field. Any suitable ferromagnetic materials from the families of iron oxides and oxide minerals can be used with the presently disclosed subject matter. Non-limiting examples of ferromagnetic materials that can be used with the presently disclosed subject matter include magnetite ($Fe_3O_4$), maghemite ($\gamma Fe_2O_3$), jacobsite ($MnFe_2O_4$), trevorite ($NiFe_2O_4$), magnesioferrite ($MgFe_2O_4$), pyrrhotite ($Fe_7S_8$), greigite ($Fe_3S_4$), feroxyhyte ($\delta FeOOH$), and combinations thereof. In certain embodiments, the membrane comprises magnetite or magnetite nanoparticles.

In certain embodiments, the present disclosure provides a method of making the polymer that forms the membrane of the presently disclosed microcapsules. In certain embodiments, the method comprises mixing a starting material with a platinum catalyst to form a mixture, then incubating the mixture to form the polymer. In certain embodiment, the starting material comprises a methylhydrosiloxane and a vinyl-terminated polydimethylsiloxane base. In certain embodiments, the starting materials comprises DMS and HMS, including any DMS and HMS as described herein. In certain embodiments, the starting material further comprises dimethylallylamine. The platinum catalyst initiates the crosslinking reaction of the starting material. In certain embodiments, the method further comprises incubating the mixture at room temperature. In certain embodiments, the method further comprises incubating the mixture at between about 50° C. and about 80° C. In certain embodiments, the method further comprises incubating the mixture at about 70° C. In certain embodiments, the method further comprises incubating the mixture for between about 1 minute and about 24 hours. In certain embodiments, the method further comprises incubating the mixture for between about 1 minutes and about 10 minutes. In certain embodiments, the method further comprises incubating the mixture for about 1 minute, about 5 minutes, about 2 hours, about 4 hours, or about 24 hours. In certain embodiments, the method further comprises incubating the mixture for about 5 minutes. In certain embodiments, the method further comprises incubating the mixture at about 70° C. for about 5 minutes.

Any suitable platinum catalyst known in the art can be used with the presently disclosed subject matter. Non-limiting examples of platinum catalysts include chloroplatinic acid, dichlorobis(triphenylphosphine)platinum(II), platinum chloride, platinum oxide, complexes of platinum compounds, and combinations thereof. In certain embodiments, the platinum catalyst is platinum-divinyltetramethyldisiloxane; 2% Pt in Xylene. In certain embodiments, the concentration of the platinum catalyst in the mixture or the presently disclosed membrane is between about 0.5 ppm and about 5 ppm. In certain embodiments, the concentration of the platinum catalyst in the mixture or the presently disclosed membrane is about 0.5 ppm, about 1 ppm, at 1.5 ppm, about 2 ppm, about 2.5 ppm, about 3 ppm, about 3.5 ppm, about 4 ppm, about 4.5 ppm, or about 5 ppm. In certain embodiments, the concentration of the platinum catalyst in the mixture or the presently disclosed membrane is about 1.5 ppm or about 3 ppm.

In certain embodiments, the present disclosure provides microcapsules comprising the polymer made by the methods disclosed herein, wherein the microcapsules remain stable for an extended period of time. In certain embodiments, the methods comprise the use of the platinum catalyst, wherein the concentration of the platinum catalyst in the mixture is about 3 ppm. In certain embodiments, the methods comprise incubating the mixture at about 70° C. for about 5 minutes.

In certain embodiments, the core comprises a molecule that is selected from the group consisting of antibiotics, quorum sensing (peptide) molecules, and glucose. Microcapsules comprise such molecules can used for delivering such drugs to a subject for preventing or treating a disorder.

In certain embodiments, the core comprises a plurality of microbes suspended in a medium, where the microcapsule functions as a microbial nanoculture capsule for culturing and/or delivering the microbes to a subject in need thereof.

In certain embodiments, the subject is susceptible or suffers from a disorder. In certain embodiments, the disorder is selected from the group consisting of *Clostridium Difficile* infection, functional bowel diseases, colorectal carcinoma, cardiovascular disease, periodontal diseases, obesity, psoriasis, reflux esophagitis, childhood-onset asthma, inflammatory bowel disease (e.g., colitis), diabetes, cancers, neuropsychiatric disorders (e.g., Alzheimer's disease, autism, depression), skin disorders (e.g., atopic dermatitis, erythrasma), ear infection, urogenital infections (e.g., bacterial vaginosis, chlamydia vaginitis, trichomonas, urinary tract infections).

The microbes can be isolated from a healthy sample obtained from a subject. In certain embodiments, the microbes are obtained from lungs, respiratory tracts, genital tracts, skin, eyes or nasal passages of the subject. The subject can be a non-human mammal or a human. The sample obtained from the subject can be a fecal sample or a sample obtained from upper intestinal tract. Following sample collection, the sample can be frozen down in glycerol, maintaining the native environment as is, and stored for future process. In certain embodiments, the microbes are isolated from soil or marine.

In certain embodiments, the medium is a culture medium comprising basic nutrients essential for the growth of microbes. Non-limiting examples of nutrients include carbon, nitrogen, phosphate, glucose and bile salt. The pH of the culture medium can be adjusted by any methods known in the art to mimic the native environment the microbe isolated from.

Any suitable methods known in the art can be used to make the microcapsules. In certain embodiments, the microcapsules can be generated using a microfluidic device, which includes a micro-scale pipette system with three inlets (Niepa T H et al., Scientific Report, 2016 Aug. 1; 6:30578). The three inlet fluids include a surfactant, an outer phase made of a soft polymer, and the inner phase, the microbe culture comprising microbes and culture medium, which meet at an interface where the microcapsules are created (FIG. 1). At this interface, the soft polymer forms the TNs, encapsulating the microbial culture inside, on the scale of nanoliters. The surfactant stabilizes the capsules in solution, until polymerization occurs. This high-throughput method can create hundreds of thousands of capsules in just ten minutes and are easily maintained for long-term delivery.

In certain embodiments, after encapsulating the microbes, the microcapsules can be stored in a 154 mM saline solution, to mimic the molarity inside human cells. This provides an isotonic environment for the microcapsules and does not induce excessive swelling or shrinking. In certain embodiments, the size of the microcapsules can be adjusted using osmotic pressures to either force water into, or out of, the microcapsules.

5.3 Applications and Uses

In another aspect, the present disclosure provides a method for restoring a healthy microbiome in a subject, comprising administering to the subject a plurality of microcapsules comprising an effective amount of probiotic microbes. Any suitable microcapsules disclosed herein can be used with this method. In certain embodiments, each of the microbial nanoculture capsule comprises: (a) a membrane comprising a crosslinked polymer, wherein the polymer comprises siloxane units; and (b) a core comprising a plurality of the probiotic microbes suspended in a medium, wherein the core is completely enclosed by the membrane.

In certain embodiments, the subject is a human subject. In certain embodiment, the subject is a human subject is susceptible to or suffer from a disorder selected from the group consisting of *Clostridium Difficile* infection, functional bowel diseases, colorectal carcinoma, cardiovascular disease, periodontal diseases, obesity, psoriasis, reflux esophagitis, childhood-onset asthma, inflammatory bowel disease (e.g., colitis), diabetes, cancers, neuropsychiatric disorders (e.g., Alzheimer's disease, autism, depression), skin disorders (e.g., atopic dermatitis, erythrasma), ear infection, urogenital infections (e.g., bacterial vaginosis, chlamydia vaginitis, trichomonas, urinary tract infections). In certain embodiments, the subject is a human subject who is susceptible to or suffers from *Clostridium Difficile* Infection (CDI), suffers from an immune-compromised disorder, or is an elderly subject.

In certain embodiments, the probiotic microbes are obtained from the subject before the subject receives an antibiotic treatment. In certain embodiments, the probiotic microbes are obtained from lungs, respiratory tracts, genital tracts, skin, eyes or nasal passages of the subject. After culturing the probiotic microbes in the microcapsules disclosed herein, the microbes are administered back to the subject after antibiotic treatment to deter colonization of opportunistic pathogens in the gut. In certain embodiments, the microcapsules are administered orally.

In another aspect, the present disclosure provides a pharmaceutical composition for use in restoring a healthy microbiome in a subject comprising the microcapsules disclosed herein, where the microcapsules comprise an effective amount of probiotic microbes. In certain embodiments, the pharmaceutical composition further comprises an acceptable carrier. "Acceptable carrier," as used herein, includes any carrier which does not interfere with the effectiveness of the biological activity of the active ingredients and/or that is not toxic to the subject to whom it is administered. Non-limiting examples of suitable carriers include phosphate buffered saline solutions, water, emulsions, such as oil/water emulsions, various types of wetting agents and sterile solutions. Additional non-limiting examples of compatible carriers can include any suitable vehicle, delivery or dispensing means or material. Such carriers can be formulated by conventional methods and can be administered to the subject at an effective amount.

In certain embodiments, the pharmaceutical composition is in a form of dissolvable pill. In certain embodiments, the pharmaceutical composition is administered orally. The microbes can be mixed with a carrier and (for easier delivery to the digestive tract) applied to liquid or solid food, or feed or to drinking water. The carrier material should be non-toxic to the microbes and the subject/patient. In certain embodiments, the carrier contains an ingredient that promotes viability of the microbes during storage. The formulation can include added ingredients to improve palatability and improve shelf-life. If a reproducible and measured dose is desired, the microbes can be administered by a rumen cannula.

In certain embodiments, the carrier comprises a diluent, adjuvant, excipient, or vehicle with which probiotic microbes are administered. In certain embodiments, the carrier can be sterile liquids, such as water and oils, including those of petroleum, animal, vegetable or synthetic origin, such as peanut oil, soybean oil, mineral oil, sesame oil and the like. In certain embodiments, the carrier can be water or aqueous solution, saline solutions and aqueous dextrose and glycerol solutions. In certain embodiments, the carrier can be a solid dosage form carrier, including but not limited to one or more of a binder (for compressed pills), a glidant, an encapsulating agent, a flavorant, and a colorant. Suitable carriers for therapeutic use are well known in the art and are described, for example, in "Remington's Pharmaceutical Sciences" by E. W. Martin, and in "Remington: The Science and Practice of Pharmacy." Lippincott Williams & Wilkins.

The choice of a carrier can be selected with regard to the intended route of administration and standard practice. In certain embodiments, oral delivery can be used for delivery to the digestive tract. In certain embodiments, oral formulations comprise additional mixtures, such as milk, yogurt, and infant formula.

In certain embodiments, solid dosages in the form of tablets are used for the delivery of the probiotic microbes by mixing the microcapsules comprising the probiotic microbes with sodium alginate, calcium carbonate, glyceryl monooleate, triethyl citrate, and acetylated monoglyceride, and hypromellose acetate succinate (HPMCAS). In certain embodiments, the pharmaceutical composition is in a form of dissolvable tablet. In certain embodiments, the pharmaceutical composition is administered orally.

In certain embodiments, microcapsules can be also administered parenterally.

The dosage of the probiotic microbes can vary depending upon the nature of the disease, the patient's medical history, the frequency of administration, the manner of administration, the clearance of the agent from the patient, and the like. In certain embodiments, the initial dose can be larger, followed by smaller maintenance doses. In certain embodiments, the dose can be administered as infrequently as weekly or biweekly, or fractionated into smaller doses and administered daily, semi-weekly, etc., to maintain an effective dosage level. In certain embodiments, a variety of doses are effective to achieve colonization of the gastrointestinal tract with the desired microbial composition, for example and not by way of limitation $10^6$, $10^7$, $10^8$, $10^9$, $10^{10}$, $10^{11}$, and $10^{12}$ CFU can be administered in a single dose. In certain embodiments, lower doses can also be effective, for example and not by way of limitation, $10^4$ and $10^5$ CFU.

The amount of probiotic preparation to be administered can be empirically determined by the treating physician to determine the optimal concentration and ratio based in the stage of disease and patient statistics (e.g., age, height, weight, etc.).

As used herein, the pharmaceutical composition can be delivered every 4, 12, 24, 36, 48, 60, or 72 hours. In certain embodiments, the treatment can last for at least about 1 week, at least about 2 weeks, at least about 3 weeks, at least about 4 weeks, at least about 5 weeks, at least about 6 weeks, at least about 2 months, at least about 3 months, at least about 6 months, or at least about 1 year.

In another aspect, the present disclosure further discloses a method for culturing microbes in vitro, comprising (a) obtaining a plurality of microbes; (b) encapsulating the plurality of microbes into a microcapsule disclosed herein; and (c) culturing the microcapsule in a suitable condition allowing the growth of the microbes. Such method would enable in vitro culture of microbes that are notoriously difficult to isolate and culture. Non-limiting examples of microbes include oral microbiome in the deep pockets of the gums (particularly in an individual suffering from advanced periodontitis), lungs and respiratory tracts, genital tracts, skin, eyes, and nasal passages. In certain embodiments, the microbes are obtained from soil or marine. As such, the method disclosed herein can be used to study and model growth dynamics, intra- and inter species relationships and competition, as well as drug discovery and the controlled growth of "unculturable" cells.

In another aspect, the presently disclosure provides kits comprising a pharmaceutical composition disclosed herein. The presently disclosure also provides kits comprising a plurality of microcapsules disclosed herein. In certain embodiments, the kit is for administering an effective amount of probiotic microbes to a patient in need thereof. In certain embodiment, the kit is for culturing microbes in vitro.

In certain embodiments, the kits disclosed herein further comprise one or more components such as instructions for use, devices and additional reagents, and components, such as tubes, containers and syringes for performing the methods disclosed above.

6. EXAMPLES

The presently disclosed subject matter will be better understood by reference to the following Example, which is provided as exemplary of the presently disclosed subject matter, and not by way of limitation.

Example 1: Optimization and Production of Therapeutic Nanocultures as Beneficial Microbial Banks for the Restoration and Preservation of the Healthy Human Microbiome The present example discloses a microfluidic-based technique for designing and creating functional Therapeutic Nanocultures (TNs); soft-shelled microcapsules encapsulating, culturing and storing a multitude of microbes for many purposes, such as drug discovery, modelling of microbial growth dynamics and the discovery of "unculturable" cells. The TNs appear as a functional microdevice, preserving microbes against biological and chemical insults that can alter the composition of the human microbiome. In this way, TNs are an alternative to restore a healthy microbiome to patients with high susceptibility to CDI, or other physical and mental disorders associated with an altered microbiome as seen in immune-compromised and elderly patients.

TNs allow researchers to model microbial growth dynamics, investigating intra- and inter-species competition through cell signaling, and hence, create "microbial banks". TN microbial banks serve to carry selected beneficial microorganisms back to the gut of the patient, restoring and preserving the healthy microbiome, thereby preventing the individual from opportunistic pathogenic disease.

As shown in FIG. 1, the TNs were generated using a microfluidic device, which included a micro-scale pipette system with three inlets. The three inlet fluids included a surfactant, an outer phase made of a soft polymer, and the inner phase, the bacterial broth culture, which met at an interface where the capsules were created. At this interface, the soft polymer formed the TNs, encapsulating the bacterial culture inside, on the scale of nanoliters. The surfactant stabilized the capsules in solution, until polymerization occurred. This high-throughput method can generate hundreds of thousands of capsules in just ten minutes, and the generated capsules were easily maintained for long-term delivery.

The ability to isolate and grow single cells that do not occur naturally outside of the human body in the TNs makes the system ideal for the study of microbial dynamics and drug discovery. This was achieved through the isolation of cells exhibiting antagonistic behavior and interactions with pathogenic cells or by generating metabolites capable of killing pathogens. This gives us the opportunity to tune the TNs, such that they only include beneficial microorganisms, unlike FMT where there is a realistic chance of receiving some undetectable pathogenic organisms. Thus, various beneficial microbiome communities isolated from a patient could be designed and preserved for on-demand delivery. The beneficial microbial bank would be administered back to the patient after an antibiotic treatment, recolonizing the gut and thwarting opportunistic pathogens, such as *Clostridium difficile*, from causing disease.

The TNs would be made in a lab environment, but could be administered to patients in many settings, including hospitals, clinics, and community-based living environments, such as housing for the elderly. Using the TNs as probiotics for susceptible groups, the risk of primary CD infection can be reduced substantially, and thus saving thousands of lives, as well as saving the U.S. health care system billions of dollars.

The present example also 1) develops a formulation (chemical composition) of the TNs facilitating cell culture under high-shear stress conditions; 2) functionalizes the TNs to enable their recovery and sorting using external forces; 3) designs a biocompatible system enabling growth in biological organisms (e.g., animals, humans); and 4) optimizes the high-throughput culture system for rapid screening of biological samples, re-inoculation and delivery of beneficial cells.

Example 2: Functional Poly(Hydrosiloxane)-Based Microbial Nanoculture Capsule

New siloxane-based membranes were designed to study microbial dynamics. A culture system referred to as nanoculture or nanoculture capsule was developed to encapsulate microbes in semipermeable membranes, which enabled the growth of challenging species in environmental conditions. The mechanical strength and the permeability of the siloxane-based membranes to signaling biomolecules, sugars, and antibiotics were explored to understand how microbial growth dynamics in the nanoculture capsule could be controlled with these molecules. The type of polymer used to form the shell membrane of the microcapsules depicts the extent of transport and mechanical properties of the capsules.

Depending on the type of materials used, crosslinking of the polymer can be achieved in variable amounts. For instance, a material such as Sylgard 184 becomes quite viscoelastic upon crosslinking; however, does not allow for diffusion of larger molecules across the membrane. This poses some obstacles when trying to study the effects of various chemical molecules on the microbes that have been encapsulated by the membrane. The present example screened a wide variety of poly(hydrosiloxane) membranes to achieve levels of permeability different from that of commercially available Sylgard 184 commonly used in the laboratory. By varying the ratio of methyl and vinyl functional groups in silanes and silicons, the crosslinking density was optimized, in terms of gaps and spaces within the membrane. Furthermore, the mechanical properties of the membranes were reinforced through the incorporation of silica nanoparticles, which enabled the nanoculture to withstand high shear stress similar to environmental conditions while maintaining transport properties essential to communication and growth. Additionally, by adding a variety of other functional groups in the form of crosslinkers on to the silicon backbone, the membrane was able to "recognize" molecules that were diffusive, as a product for delivery.

Products of interested in studying diffusivity across the membrane include, for example, antibiotics, quorum sensing (peptide) molecules, glucose, and water. By changing the functional groups within the membrane, properties such as wettability, hydrophobicity and hydrophilicity, oleophobicity, as well as the reactivity of the membrane with specific molecules, were tuned. For example, the addition of amines, ketones, and benzene rings, all common functional groups in antibiotics, had a beneficial effect on the permeability of the drugs that are currently in use to fight bacterial infection. Furthermore, crosslinking density depicts the mechanical properties of the membrane, such that precise shear and pressure forces needed to burst the capsules can be determined. Depending on the functionality of the capsules, for example the release of encapsulated drug, the present disclosure determines whether a quick burst-release or rather a slow-release that is tightly controlled is needed. Controlling properties such as permeability, diffusion, and mechanical strength allows the opportunity to create personalized nanocapsules.

The versatility of this nanocapsule technology lends itself to an array of different situations in which they can be used to isolate, culture, and preserve microbes from many environments. One such example is using the TNs as a microbial bank for *Clostridium difficile*, whereby the isolated healthy sample collected from the patient would be cultured and then administered back to the patient after antibiotic treatment to deter colonization of opportunistic pathogens in the gut. Depending on the specific environment within the gut to culture and store, there are a number of options for obtaining the sample. In most instances, a fecal sample would suffice; however, a sample from the upper intestinal tract can be obtained through an NG tube. Following sample collection, the sample would be frozen down in glycerol, maintaining the native environment as is. The medium used to culture the cells includes a minimal broth solution that contains all the basic nutrient sources required by microbial cells, such as carbon, nitrogen, phosphate, glucose and bile salts. The pH of media can also be easily changed, according to that of the native environment. After encapsulating the microbial cells, the capsules are stored in a 154 mM saline solution, to mimic the molarity inside human cells. This provides an isotonic environment for the capsules and does not induce excessive swelling or shrinking. However, the size of the capsules can be manipulated using osmotic pressures to either force water into, or out of, the capsules. The stored capsules are then administered back to the patient, in the form of an oral, dissolvable pill. Slow release of the capsules would ensure that the microbes are released back into the gut and not beforehand (see FIG. 1).

Likewise, this system can be used to encapsulate microbes from environments that are notoriously difficult to isolate and culture, such as the oral microbiome in the deep pockets of the gums, particularly in an individual suffering from advanced periodontitis. In this instance, a large percentage of the native oral microbiome cannot be cultured in the lab using conventional methods. Thus, the presently disclosed TNs serve as nanoscale culture flasks, whereby it can mimic the native environment, isolate and hence, culture the cells that have yet to be cultured in the lab using traditional suspension or plating methods. Following culturing of the oral microbiome, the growth dynamics of intra- and inter-species relationships can be studied, to determine anti-pathogenic mechanisms and harness chemical molecules produced by the local beneficial microbes, so as to inhibit growth of pathogenic microbes. This system can be extended to a multitude of environments, such as the microbiome of the lungs and respiratory tracts, genital tracts, skin, eyes and nasal passages, etc.

The potential of the TNs to be used in a multitude of applications is quite limitless. Beyond using the TNs in health settings, it can be used to isolate and culture microbiomes from other environments too, such as soil and marine microbiomes. The TNs can be used to study and model growth dynamics, intra- and inter species relationships and competition, as well as drug discovery and the controlled growth of "unculturable" cells.

Example 3: Functional Poly(Hydrosiloxane)-Based Microbial Nanoculture Capsules and Systems A copolymer was generated by crosslinking a methylhydrosiloxane with a vinyl-terminated polydimethylsiloxane base. The generated co-polymer formed the membrane of an embodiment of the presently disclosed therapeutic nanocultures (TNs) (also called nanoculture capsules or nanocultures herein). The methylhydrosiloxane acts as a reducing agent that induces the saturation of the vinyl-terminated polydimethylsiloxane base with the use of a platinum catalyst. This reaction results in an optically clear, hydrophobic elastomer, which is brittle in nature with little conductive properties. The presently disclosed copolymer can be further functionalized and optimized for downstream application. The functionalization and optimization can be achieved by changing the ratio of functional groups that were reacting during the curing process of the polymer. The optimization of functional group concentrations allows the manipulation of the elastomeric properties of the membrane. For example, the present disclosure discovered that decreasing the concentration of vinyl group increased the saturation of the vinyl-bonds, which resulted in a polymer membrane that had increased brittleness. This functionalization can be used to the researcher's advantage when lysing open the capsules for downstream processing. On the other hand, increasing the concentration of vinyl group can reduce the occurrence of cross-link and the saturation of the vinyl-bond, thus generating a polymer membrane that has increased elasticity. Membrane that is more brittle results in more efficient downstream processing, because the TNs are more prone to mechanical lysing methods, such as mechanical bead-beating, thereby releasing the contents of the TNs into solution which can go on for downstream processing. In contrast, membrane that is more elastic has improved response to hydrodynamic pressures, and is less prone to lysing by mechanical means, making downstream processing more of a challenge and less efficient.

The presently disclosed membranes were further functionalized to promote their use in various applications. For example, the inclusion of dimethylallylamine (DMAA) to the presently disclosed membrane decreased the hydrophobicity and increased the hydrophilicity of the membrane. Increasing hydrophilicity can promote the permeability and diffusion properties of the membrane, thus assisting in studying the communication signals between the internal and external environments of the TNs. This allows for the microorganisms to still receive signals from their native environments whilst remaining under close study within the controlled TN environment.

The presently disclosed membranes were also functionalized by adding magnetite, an iron ore that is ferromagnetic. This magnetic functionalization allowed for the controlled movement of TNs. For example, if the TNs are disseminated into a soil or marine environment for study, they can easily be retrieved with the use of a magnetic field.

The present disclosure experimentally characterized the presently disclosed membranes by using Fourier-Transform Infrared Spectroscopy (FTIR, absorbance and transmittance) to assess polymers having various compositions, using contact angle measurements to assess wettability, and using stability experiments in the case of encapsulation of the polymer with growth of bacteria in proof-of-concept experiments.

An embodiment of the presently disclosed membrane was synthesized. Starting materials, including HMS-053 (0.9 g), DMS-V21 (1.9 g) and platinum catalyst (97.2 µL) were mixed, with an end concentration of 3 ppm platinum in the solution. The polymer components were mixed in a weigh boat and spin coated over a Silicon wafer (1 min at 750 rpm) using a Laurell WS-650-23. The membrane was cured at 70° C. for 3 hours.

HMS-053 and DMS-V21 (the two starting reagents), were mixed and cured using a platinum catalyst to form the final version polymer, PDMS(53-21), which was an embodiment of the presently disclosed polymer. The ratio of functional groups ranged from (H:V)=(0.6:1) to (1:1).

DMS-V21 is the product code for Vinyl Terminated Polydimethylsiloxane that is commercially available. DMS-V21 provided the base polymer that was crosslinked with HMS-053. This starting polymer provided terminal vinyl (C=C) functional groups, the concentration of which was calculated to determine the necessary ratio of end-point functional groups. The double C=C bond was reduced to C—C saturated bond when crosslinked with HMS-053. HMS-053 is the product code for (4-6%-Methylhydrosiloxane)-Dimethylsiloxane Copolymer, Trimethylsiloxane Terminated.

The amounts of DMS-V21 and HMS-53 used in the present example were calculated based on the concentration of functional groups used as crosslinkers in the final polymer. HMS-053 was used as the reducing agent within the reaction; hence, the functional group of interest was hydrogen which acted as a proton donor. The concentration of this functional group was then matched to the concentration of the functional group in the second starting reagent (DMS-V21), and their ratios were adjusted as necessary to obtain a polymer blend with the correct composition for its application. The ratios of functional groups can range between (H:V)=(0.6:1) and (1:1), where H:V represented the ratio between hydride groups to vinyl groups. The more vinyl C=C bonds that are left un-crosslinked, the more elastic the polymer. Hence, having a smaller ratio of (H:V), such as (0.6:1), results in a more elastic polymer, whereas a ratio of (1:1) results in complete saturation of the vinyl C=C bond; therefore, the resulting polymer is more brittle and has less elasticity.

PDMS(53-21) (Polydimethylsiloxane 53-21) was the final polymer composed of MethylHydrosiloxane (HMS)-053 and polydimethylsiloxane (DMS)-V21, with the use of a platinum catalyst to induce crosslinking and hence, curing of the polymer.

A representative image of the synthesized membrane is shown in FIG. 2A. The absorbance spectra of the synthesized polymer PDMS (53-21) showed the disappearance of the vinyl bond as compared to HMS-053 and DMS-V21 (FIG. 2B). The peak of interest at approximately 910 cm$^{-1}$ showed the remnants of the vinyl C=C double bond, which became saturated to a C—C single bond as crosslinking progressed. The double vinyl C=C functional group in DMS-V21 was apparent in the IR-spectrum that corresponds to only DMS-V21, which showed a peak at approximately 910 cm$^{-1}$ (FIG. 2B). This peak was lacking in HMS-053, which did not have a double C=C bond, and was also minimized in the IR-spectrum that corresponds to PDMS (53-21), signifying that crosslinking saturated the C=C double bonds to form C—C single bonds in the final version of the polymer, PDMS(53-21).

Stability of capsules was calculated by manually counting the number of capsules that remained as capsules throughout the timed experiment. Capsules were imaged under a microscope (Zeiss Axioscope) over a period of time (15 hours at 30 second intervals) and capsules that popped were counted. This was converted to a percentage, whereby the number of remaining capsules resulted in the percentage of stable capsules. Stability of the presently disclosed nanoculture capsules were optimized by tuning the concentration of platinum in the membrane (FIG. 3A).

Immediately following the encapsulation process, the capsules were placed into a 70° C. oven for 5 minutes, followed by room temperature, or they did not have heat treatment at all and were simply cured at room temperature. Heat treatment improved the mechanical properties of the presently disclosed nanoculture capsules (FIG. 3B).

Additionally, treating the presently disclosed capsules at 70° C. for increased time periods improved the strength and stability of the nanoculture capsules (FIG. 3C). PDMS(53-21) microcapsules were treated with varying times of heat treatment (signified by the curing time), at 70° C. Hence, capsules were stored at 70° C. for 0 minutes, 5 minutes, 2 hours, 4 hours and 24 hours, to determine effects of heat treatment on stability of the capsules. Heat treatment for 5 minutes resulted in stable capsules. The capsules were then subjected to a 1 M hypertonic NaCl solution, inducing significant osmotic pressure on the capsules, resulting in water osmosing out of the capsules. The capsules behaved differently according to their state of crosslinking. Capsules that were fully crosslinked resulted in buckling (as seen after the 2 h curing time panel). Osmotic pressures can be used to calculate the Young's modulus of the capsules. Ratio of functional hydride groups to functional vinyl groups was calculated based on the concentration of functional groups in the starting reagents. It was discovered that capsules treated at 70° C. for 5 minutes remained entirely stable.

Nanoculture capsules were generated with the presently disclosed polymer mixture. Representative fluorescent images were taken 24 hours after the capsules were incubated at 37° C. The fluorescent dye Nile Red was mixed into the DMS-V21 at a concentration of 40 ug/mL, before mixing with HMS-053. Nile Red is soluble in DMS-V21. The generated nanoculture capsules remained stable after incubation at 37° C. for 24 hours (FIG. 4).

The presently disclosed polymer was used in proof-of-concept experiments to determine successful bacterial growth and stability of the capsules over a 24-hour period. *Escherichia coli* (*E. coli.*) were enclosed and grew within the capsules (FIG. 5A). During the manufacturing process, the polymer was stained with Nile Red, a lipophilic fluorescent dye for staining cellular membranes. Nile Red was also used to determine kinetic diffusion properties of the presently disclosed membranes. *E. coli* tagged with green fluorescent protein (GFP) was used as the bacterial inoculum for the inner phase of the capsules. Fluorescent images confirmed confluent growth of cells within the nanoculture capsules (FIGS. 5B-5C). Successful bacterial growth supported the use of the nanoculture capsules for culturing fastidious species, studying native microbiomes, and determining population dynamics.

To further functionalize the presently disclosed nanoculture capsules, DMAA (an amine) was introduce in the membrane of the nanoculture capsules to decrease the hydrophobicity of the membrane (FIG. 6). Inclusion of DMAA in the polymer membrane of the nanoculture capsules enlarged the size of the holes in the crosslinked network, thus increased the size of the molecules that were allowed to diffuse across the membrane. "% DMAA in Vinyl" referred to the percentage (or ratio) of moles of functional group of DMAA to the moles of functional group of (DMAA+DMS-V21). Both the DMAA and DMS-V21 has a vinyl group as the functional group. Hence, the same reaction is occurring between DMAA and HMS-053 and between DMS-V21 and HMS-053, but the chain length of DMAA is drastically smaller than DMS-V21 (in the order of $10^2$) and therefore, creates holes in the cross-linked membrane. The % DMAA implicitly relates to the number of holes in the membrane, or the degree of polymerization. When the reaction between the hydride (functional group of HMS-053) and vinyl (functional group of DMAA and DMS-V21) happens, the saturation of the C=C vinyl bonds can be observed at around 910 cm$^{-1}$ in the IR spectra, which was highlighted in the enlarged window. The intensity of the peaks was proportional to the % of DMAA. 90% DMAA, according to the IR-spectra, signified the prevalence of the vinyl C=C double bonds, indicating that crosslinking was occurring to a lesser extent. The resulting membrane with 90% DMAA was not fully cured, compared to that of 15% DMAA. The presently disclosed membranes that contained different concentrations of DMAA were further tested for their permeability of a larger variety of molecules.

Concentration of DMAA was increased in the presently disclosed membrane to determine increase in wettability. Wettability was measured by contact angle measurement. Water and ethanol were used as liquid phase solvents against the presently disclosed polymer membranes. Increasing the concentration of DMAA in the membrane resulted in an increased hydrophilic surface in both solvents. With regards to the membrane having a 1:1 ratio of hydride to vinyl functional groups, the wettability was increased by a maximum of 5% in the case of water, and 19% in the case of ethanol (FIG. 7).

The presently disclosed polymer was used in encapsulation experiments to determine the stability of the polymer for its applied use. Encapsulation was performed with distilled water as the inner phase and the collecting medium, under two sets of operating conditions: amount of Pt catalyst—1.5 ppm and 3 ppm, and preparatory heat treatment at 70° C. First, the encapsulation was performed with 1.5 ppm Pt (overall concentration of Pt in the final PDMS(53-21) polymer), where one of the samples was subjected to a 5-minute heat treatment at 70° C. immediately after encapsulation, while the other was not, to determine if heat had any effect on the capsules or not. A 15-hour observation of these capsules at room temperature showed that the sample subjected to heat treatment had a relatively better survivability rate than the other. Increasing the concentration of Pt to 3 ppm showed the same trend but with a higher number of capsules surviving the duration of observation. Extending the same experimental conditions to the DMAA functionalized PDMS (53-21) showed a 100% survivability of the microcapsules. Stability of capsules was calculated by manually counting the number of capsules that remained as capsules throughout the timed experiment. Capsules were imaged under a microscope (Zeiss Axioscope) over a period of time (15 hours at 30 second intervals) and capsules that popped were counted. This was converted to a percentage, whereby the number of remaining capsules resulted in the percentage of stable capsules.

Glass microfluidic devices were used to create the polymer microcapsules, which were then either treated with heat, or were not, to determine if heat had an effect on the polymer microcapsules. A minimum of 3 ppm platinum catalyst, in conjunction with the 5 minute heat treatment at 70° C. generated microcapsules that remained 100% stable in an overnight experiment. Including 15% DMAA in the polymer composition did not affect the survivability of the capsules, hence, use of the hydrophilic molecule in the polymer does not affect stability of the capsules (FIG. 8).

The presently disclosed polymer was used to investigate the diffusion of antibiotic molecules through the membrane. *Pseudomonas aeruginosa* strain PAO1 was used as the bacterial inoculum for the inner phase of the nanoculture capsules. Antibiotics, including tobramycin and tetracycline, to which the PAO1 were sensitive, were introduced 24 hours after encapsulation. A 24-hour incubation period allowed for the confluent growth of PAO1. As compared with the nanoculture capsules that were not treated with tobramycin (FIG. 9A), PAO1 cells persisted in nanoculture capsules treated with 50 ug/ml tobramycin, indicating that tobramycin was unable to permeate and diffuse through the membrane (FIG. 9B). In contrast, PAO1 cells were completely killed in nanoculture capsules treated with 50 ug/ml tetracycline, indicating that tetracycline is able to diffuse through the membrane. Microcapsules used in FIGS. 9A-9C were generated by using (H:V)=(0.6:1) with 3 ppm Pt catalyst and 0% DMAA. The generated microcapsules were heat treated for 5 minutes at 70° C. immediately after encapsulation. Following heat treatment, capsules were incubated at 37° C. for 24 hours.

Although the presently disclosed subject matter and its advantages have been described in detail, it should be understood that various changes, substitutions and alterations can be made herein without departing from the spirit and scope of the invention. Moreover, the scope of the present application is not intended to be limited to the particular embodiments of the process, machine, manufacture, and composition of matter, means, methods and steps described in the specification. As one of ordinary skill in the art will readily appreciate from the invention of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Various patents, patent applications, publications, product descriptions, protocols, and sequence accession numbers are cited throughout this application, the inventions of which are incorporated herein by reference in their entireties for all purposes.

What is claimed is:

1. A microcapsule comprising:
   (a) a membrane comprising a crosslinked polymer, wherein the crosslinked polymer comprises siloxane units, wherein the membrane comprises dimethylallylamine; and
   (b) a core comprising a plurality of microbes suspended in a medium,
   wherein the core is completely enclosed by the membrane.

2. The microcapsule of claim 1, wherein the siloxane units are methylhydrosiloxane units.

3. The microcapsule of claim 1, wherein the crosslinked polymer is generated by crosslinking a starting material comprising hydride groups and vinyl groups, wherein the ratio between the hydride groups and the vinyl groups in the starting material is between about 0.5 and about 1.

4. The microcapsule of claim 3, wherein the starting material comprises a methylhydrosiloxane and a vinyl terminated polydimethylsiloxane.

5. The microcapsule of claim 4, wherein the methylhydrosiloxane is (4-6% methylhydrosiloxane) dimethylsiloxane copolymer, trimethylsiloxane terminated.

6. The microcapsule of claim 4, wherein the vinyl terminated polydimethylsiloxane comprises 0.8-1.2 wt % vinyl and has a molecular weight (MW) of about 6000 g/mol.

7. The microcapsule of claim 1, wherein the membrane further comprises a ferromagnetic material.

8. The microcapsule of claim 1, wherein the plurality of microbes is obtained from a mammal or a human.

9. The microcapsule of claim 1, wherein the microbes comprise probiotic microbes.

10. A method for restoring a healthy microbiome in a subject, comprising administering to the subject a plurality of microcapsules comprising an effective amount of probiotic microbes,
    wherein each of the microcapsule comprises: (a) a membrane comprising a crosslinked polymer, wherein the crosslinked polymer comprises siloxane units; and (b) a core comprising a plurality of the probiotic microbes suspended in a medium, wherein the core is completely enclosed by the membrane, wherein the membrane comprises dimethylallylamine.

11. The method of claim 10, wherein the probiotic microbes are obtained from the subject before the subject receives an antibiotic treatment, or after the subject receives the antibiotic treatment.

12. The method of claim 10, wherein the subject is susceptible to *Clostridium difficile* Infection (CDI), suffers from an immune-compromised disorder or is an elderly patient.

13. A method for culturing microbes in vitro, comprising:
    (a) obtaining a plurality of microbes;
    (b) encapsulating the plurality of microbes into a microcapsule of claim 1; and
    (c) culturing the microcapsule in a suitable condition allowing the growth of the microbes.

14. A kit comprising a plurality of microcapsules of claim 1.

* * * * *